United States Patent [19]
Kushida et al.

[11] 3,958,721
[45] May 25, 1976

[54] COLLAPSABLE TUBE

[76] Inventors: Hideo Kushida; Yoshio Hara; Toshie Tanaka; Takeshi Itakura, all of c/o Yoshino Kogyosho Co., Ltd., 2-6, Oojima 3-chome, Koto, Tokyo, Japan

[22] Filed: Jan. 15, 1973

[21] Appl. No.: 323,982

[30] Foreign Application Priority Data
Jan. 18, 1972 Japan.......................... 47-8656[U]

[52] U.S. Cl. ............................................... 222/107
[51] Int. Cl.² ........................................ B65D 35/10
[58] Field of Search.................. 222/107, 491, 494; 156/90; 117/161 UE

[56] References Cited
UNITED STATES PATENTS

| | | | |
|---|---|---|---|
| 2,430,046 | 11/1947 | Dreyfus............................. | 222/107 |
| 3,172,571 | 3/1965 | Marchak........................... | 222/107 |
| 3,178,065 | 4/1965 | Averswald ........................ | 222/107 |
| 3,179,300 | 4/1965 | Davidson et al. ................ | 222/494 X |
| 3,347,419 | 10/1967 | Brandt et al. .................... | 222/107 |
| 3,381,818 | 5/1968 | Cope et al. ...................... | 222/107 X |
| 3,505,143 | 4/1970 | Haas et al. ...................... | 222/107 X |

FOREIGN PATENTS OR APPLICATIONS

| | | | |
|---|---|---|---|
| 298,095 | 6/1932 | Italy.................................. | 222/494 |

OTHER PUBLICATIONS

E. I. DuPont de Nemours & Company, "Elvanol Polyvinyl Alcohol," Mar. 13, 1950.

Handbook of Plastics; Simonds, Weith, and Bigelow; Jan. 1949; pp. 64–67, 70–71, 77–78, 427–429.

*Primary Examiner*—Robert B. Reeves
*Assistant Examiner*—Joseph J. Rolla

[57] ABSTRACT

A collapsable tube of synthetic resin materials and adapted to prevent oxidization of the substance contained therein. The body of the tube is constructed of a laminated sheet which, in one embodiment, comprises a polyethylene film an oriented polypropylene film, a polyvinyl alcohol film and a polyethylene film in the order named. Due to the provision of the polyvinyl alcohol film the sheet has an extremely low permeability to oxygen gas and odour and is highly resistant to oil. The oriented polypropylene film provides for the sheet increased rigidity as well as improved printability. A non-return valve is provided at the tube orifice in order to prevent the entrance of air thereinto thus causing substantially no oxidization of the substance contained.

22 Claims, 16 Drawing Figures

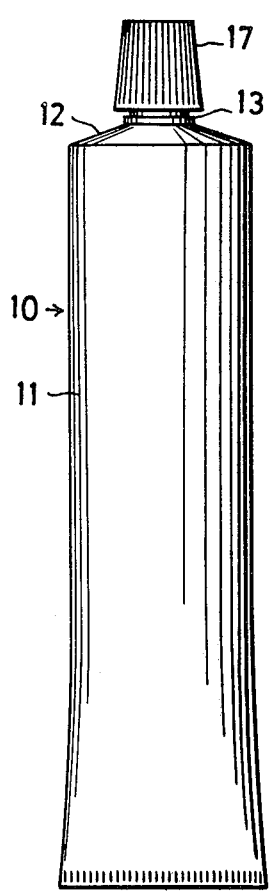
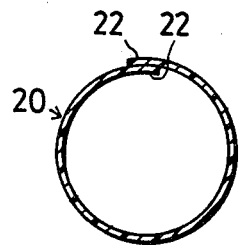
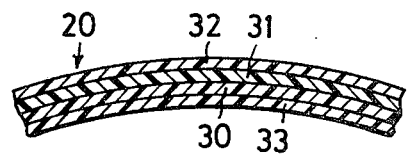
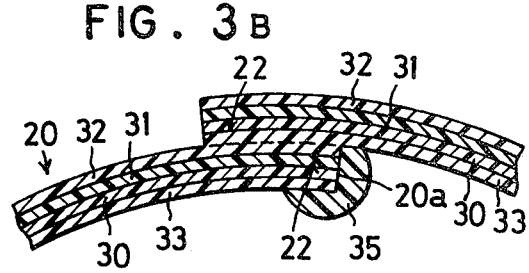
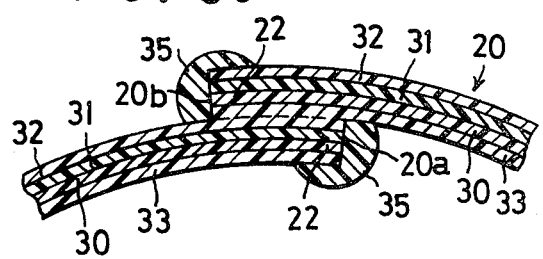
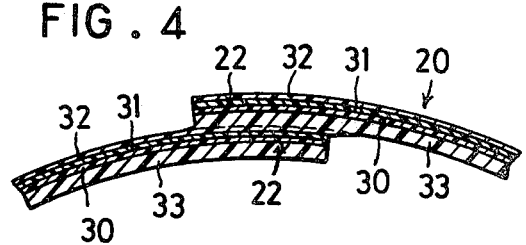

COLLAPSABLE TUBE

This invention relates to collapsable tubes and more particularly to such tubes which are formed of synthetic resin materials and which are of such a construction as to prevent oxidization of the substance contained therein.

To date, there are different tubes available for holding tooth paste, medicinal paste, paste food or the like. Most of these tubes, in the past, were formed of metal such as aluminium with the accompanying disadvantage that the body thereof was left ugly without returning to its original shape after having been compressed. Recently, collapsable tubes which are formed of synthetic resin materials have been in common use because of numerous advantages offered such as reduced cost and increased productivity. However, these tubes allow air to enter into the body thereof during returning to its original shape and the air tends not only to oxidize the substance contained but also to cause it to splash when the body is rapidly compressed. Further, there is a general tendency for synthetic resin tubes to have a relatively high permeability rate for oxygen gas, water vapour and odour as well as to exhibit a poor oil-resisting property, which leads to oxidization, weight loss, odour loss and drying of the substance contained therein.

It has been found that a polyvinyl alcohol film has an extremely low permeability to oxygen gas and odour and in addition is highly resistant to oil. The collapsable tube which is constructed of a sheet of the polyvinyl alcohol film and water-resistant polyethylene films coextensively disposed on both surfaces thereof has proved quite satisfactory. However, the polyvinyl alcohol film has the disadvantage of poor printability which is critical to its use as a packaging medium for commercial products such as, for example, tooth paste. Further, the collapsable tube of the conventional construction cannot prevent the entrance of air thereinto through its orifice after having been compressed.

It is therefore an object of the invention to provide an improved collapsable tube with a view to overcoming the above-stated disadvantages.

Another object of the invention is to provide an improved collapsable tube in which the body portion thereof is constructed of a sheet of laminated synthetic resin films including a polyvinyl alcohol film and a printable film made of, for example, oriented polypropylene.

It is a further object of the invention to provide an improved collapsable tube including a non-return valve which acts to prevent the entrance of air thereinto through the orifice to thereby preventing oxidization of the substance contained in the tube.

These and other objects will be readily apparent from the following description of the invention when taken in conjunction with the accompanying drawings, in which:

FIG. 1 is an elevation showing a collapsable tube of the invention;

FIG. 2 is a cross section showing the body of the tube;

FIG. 3A is an enlarged fragmentary cross section showing a sheet of laminated synthetic resin films of which the body of the tube is constructed;

FIG. 3B is a fragmentary, enlarged cross section showing the manner in which a molten, water-resisting material such as polyethylene is applied to the inner end surface of the sheet;

FIG. 3C is a view similar to FIG. 3B showing the manner in which the molten, water-resisting material is applied on each end surface of the sheet;

FIG. 4 is a view similar to FIG. 3A, showing another embodiment of the invention;

Figure 5:
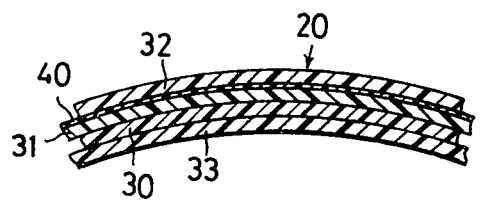
FIGS. 5, 6 and 7 are enlarged fragmentary cross sections showing various sheets of laminated films of which the tube is formed.

Referring now to FIG. 1, reference numeral 10 designates generally a collapsable tube constructed in accordance with the present invention. The tube 10 includes a body 11, a shoulder 12 and a neck portion 13, the shoulder and the neck being formed integrally with each other to form a head. The neck portion 13 has a screw thread formed thereon for removably mounting a cap 17. The lower end of the body 11 is sealed in the manner as shown in FIG. 1, but may be secured to the periphery of a suitable bottom member (not shown). The sealing may usually be effected after the tube is completely filled with its content.

In the fabrication of the collapsable tube 10, the body 11 is formed in a generally cylindrical shape by bending a sheet 20 of laminated films with the side end portions 22 overlapping each other, as is best seen in FIG. 2. The side end portions 22 are then sealed by electric heating or any other suitable method. Thereafter, the cylindrical body 11 is secured or welded at its end to the periphery of the shoulder 12 having the neck 13 integrally formed therewith.

In FIG. 3A, there is shown a typical example of the sheet 20 employed in forming the body 11 of the tube 10. In this embodiment, the sheet 20 comprises a polyvinyl alcohol film 30, a printable film 31 coextensively disposed on the outer surface of the film 30, an outer polyethylene film 32 coextensively disposed on the outer surface of the printable film 31, and an inner polyethylene film 33 coextensively disposed on the inner surface of the polyvinyl alcohol film 30.

As is well known in the art, a polyvinyl alcohol film has an extremely low permeability to oxygen gas and odour and, in addition, is highly resistant to oil. Since, however, the polyvinyl alcohol film is water-soluble and has a poor printability, the printable film 31 is disposed on the polyvinyl alcohol film 30 and thereafter the two water-resisting polyethylene films 32 and 33 are disposed on the outer and inner surfaces of the intermediate layers. In addition to improved printability, the printable film provides increased rigidity for the tube 10, thereby providing for easy filling and better handling on automatic wrapping, pouch-packaging and similar equipment.

Instead of polyvinyl alcohol, the film 30 may be comprised of vinyl alcohol copolymers such as, preferably, an ethylene-vinyl alcohol copolymer. Since this particular vinyl alcohol copolymer has been found water-insoluble, the collapsable tube including a layer of the material offers increased water-resisting property.

The printable film 31 may be comprised of oriented polypropylene, nylon, polyester, paper or any other suitable material. A film of oriented polypropylene is considerably stiff so that the collapsable tube including a layer of the material offers increased rigidity. Further, it has been found that the oriented polypropylene film has an excellent printability, but it is necessary to subject the film to surface treatment before being printed. Also, in the case when nylon is used to comprise the printable film 31, the sheet 20 offers excellent printability. If it is desired to use paper, it is necessary that the paper be coated with coatings of polyethylene to provide adhesiveness to the first polyethylene film 32 and the polyvinyl alcohol film 30. Moreover, it would be possible to use two or more of the above-mentioned materials to form the printable layer 31, such as a combination of oriented polypropylene and paper, or that of nylon and paper, or that of oriented polypropylene and nylon.

The polyethylene films 32 and 33 are used to add the water-resisting property to the sheet 20. If desired, polypropylene, polyvinyl chloride or the like may be used in place of polyethylene.

FIG. 3B shows the manner in which a molten, water-resisting material 35 such as polyethylene is applied to the inner end surface 20a of the sheet 20. By so doing, it is possible not only to prevent the end of the water-resisting polyvinyl alcohol film 30 from exposure to the substance to be contained in the tube 10 but also to prevent deterioration of adhesiveness among the layers which would otherwise result from the fact that an adhesive material flows into the substance contained during a long time use. If desired, such as a water-resisting material 35 may also be applied to the outer end surface 20b of the sheet, as is shown in FIG. 3C.

In FIG. 4, there is shown one preferred embodiment of the present invention in which the inner polyethylene film 33 is approximately 1.5 to 4 times as thick as the outer polyethylene film 32. In this embodiment also, the sheet 20 comprises the outer polyethylene film 32, the printable film 31 such as an oriented polypropylene film, the polyvinyl alcohol film 30 and the inner polyethylene film 33 in the order named. One advantage to be realized through provision of the thick polyethylene film 33 is that the sheet 20 can be formed in a strictly circular cylindrical shape with readiness, thus facilitating joining the shoulder 12 to the upper end of the body 11. Further, there is little likelihood that exfoliation or separation of the films or layers takes place especially between the oriented polypropylene film 31 and the outer polyethylene film 32 when the sheet 20 is bent to form a cylindrical body, since the inner, thick polyethylene film 33 is subject to a major portion of bending stress. In forming the cylindrical body portion 11, the sheet 20 is bent with the inner, thick polyethylene film 33 in surface engagement with the outer, thin polyethylene film 32 at their side ends, as is best seen in FIG. 4. Thus the polyvinyl alcohol film 30 has only a little thermal hysteresis after the sheet 20 is heat sealed. Accordingly, adhesiveness is not deteriorated and there occurs little or substantially no exfolization or separation of the films due to heat added.

In FIG. 5, there is shown another example of the sheet 20 of which the body 11 is constructed. In this embodiment, the oriented polypropylene film 31 is coated on its outer surface with a coating 40 of polyvinylidene chloride. Provision of the coating or layer 40 of polyvinylidene chloride serves to improve adhesiveness between the oriented polypropylene film 31 and the outer polyethylene film 32, both of which would otherwise be jointed to each other with inherent reduced adhesiveness. It has been found that a coating of polyvinylidene chloride has a relatively low permeability rate for oxygen gas and the rate varies only slightly as humidity changes. Thus, by the addition of the polyvinylidene chloride coating 40 it is possible to compensate for the increase in oxygen gas permeability of the polyvinyl alcohol film 30 occurring at high humidities. In other words, although the polyvinyl alcohol film 30 is protected against water by the outer and inner polyethylene films 32 and 33, the polyvinyl alcohol film will absorb water or moisture penetrating the polyethylene films after a long time use, resulting in the increase in oxygen gas permeability. Since, however, the rate of oxygen gas permeability of the polyvinylidene chloride coating 40 remains substantially unchanged irrespective of humidity, the sheet 20 including these two layers exhibits a low oxygen gas permeability over a wide range of humidity. Further, it has been found that the oriented polypropylene film 31 with the polyvinylidene chloride coating 40 has approximately one half the water permeability of the film 31 having no such coating thereon, thus providing improved moisture-proof property for the sheet 20. Although, in this embodiment, it is the oriented polypropylene film that is coated with a coating of polyvinylidene chloride, it should be noted that a polyester film may instead be coated with such a coating to provide the above-stated advantages. Further, it should be noted that it would be useful to coat the polyvinyl alcohol film 30 with the coating of polyvinylidene chloride.

Figure 6:
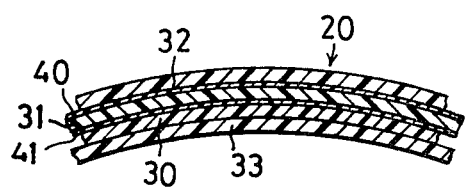
Figure 7:
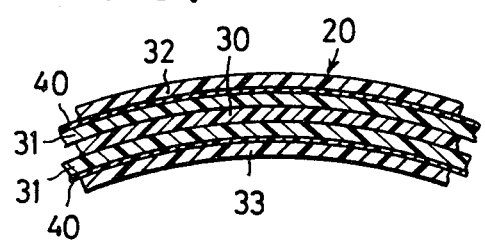

It will be appreciated that the oriented polypropylene or polyester film 31 may advantageously be coated on both surfaces thereof with coatings 40 and 41 of polyvinylidene chloride, as is shown in FIG. 6. Further, it would also be advisable to interpose another oriented polypropylene or polyester film 31 having a coating of polyvinylidene chloride between the polyvinyl alcohol film 30 and the inner polyethylene film 33, as is shown in FIG. 7.

Although, as described above, the collapsable tube 10 of the invention has numerous advantages over the prior art ones, such as, for example, an extremely low permeability to oxygen gas, water vapour and odour, it would be extremely difficult to prevent the substance contained in the tube from being oxidized by the air entering through the orifice when the body returns to its original shape after having been compressed to squeeze out the substance.

Figure 8:
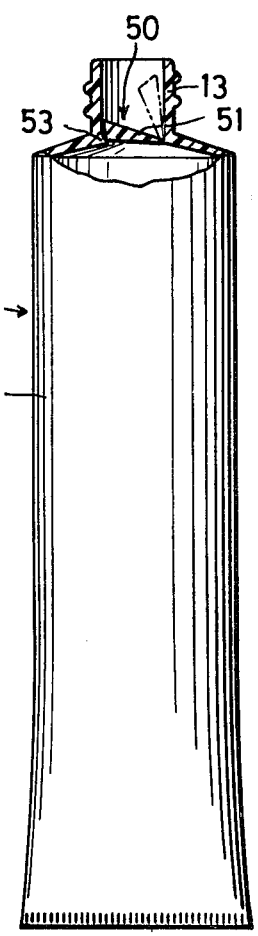
FIG. 8 is a partially-sectioned view showing a non-return valve provided at the neck portion of the tube.

The present invention also contemplates provision of a nonreturn valve at the orifice of the collapsable tube 10 to prevent the entrance of air thereinto, thereby preventing the oxidization of the substance contained in the tube. FIG. 8 shows one example of the nonreturn valve 50 which comprises a generally circular valve member 51 formed integrally with the neck portion 13. Although not specifically shown, the valve member 51 is elastically connected only in a limited circumferential portion thereof with the inner surface of the neck. In the particular circumferential portion, the valve member 51 is made relatively thin so that it can readily be bent from the position indicated by the solid line to that indicated by the broken line when the substance contained in the tube 10 is squeezed out. However, when pressures developed inside the tube 10 are released, the valve member 51 automatically returns to the position indicated by the solid line due to its elasticity. In this position, the remaining circumferential portion of the valve member 51 is held substantially in sealing contact with a corresponding inward projection 53 formed on the inner surface of the neck 13. The inward projection 53 acts to prevent the valve member 51 from moving or rotating in a counterclockwise direction from the position indicated by the solid line. Although, in this embodiment, the valve member 51 is formed integrally with the neck portion 13, it will be appreciated that the valve member may be jointed to a cylindrical body which is fitted into the neck portion 13.

Figure 9:
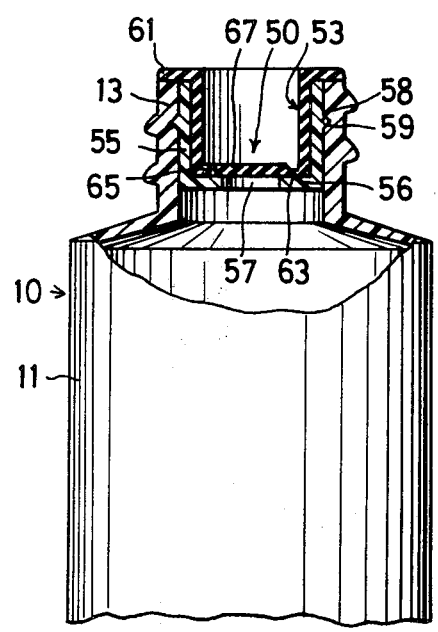
FIGS. 9, 10 and 11 show another form of the non-return valve.
Figure 10:
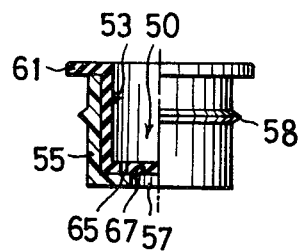

FIG. 9 shows another example of the non-return valve 50 comprising a valve member 53 and a valve body 55, both of which are constructed of suitable plastic material. The valve body 55 is in the form of a cylinder and has an outer diameter substantially the same as or slightly larger than the inner diameter of the neck portion 13 so that it can be fitted into the neck. The valve body 55 has a bottom portion 56 formed with a central opening 57, and is also provided on its outer periphery with a projection 58 (see FIG. 10) which is adapted to be received in a corresponding peripheral groove 59 formed in the inner surface of the neck 13 to prevent relative movements of the valve body and the neck.

Figure 11:
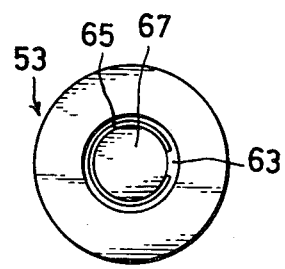

The valve member 53 is also in the form of a cylinder and has a radially outwardly extending flange 61 formed on top of it. The outer diameter of the valve member 53 is determined to be substantially identical to or slightly larger than the inner diameter of the valve body 55. As is best seen in FIG. 11, the valve member 53 includes a bottom portion 63 having a generally annular opening 65 formed therein. The annular form of the opening 65 is not quite complete, a break being provided so that the inner circular portion 67 is elastically connected to the body. As is best seen in FIG. 9, the bottom of the valve body 55 is grooved or made relatively thin at the break portion to permit ready upward movement of the inner circular portion 67 when the substance contained in the tube is forced out through the opening 57 in the valve body 55. Thus, it will be understood that the diameter of the opening 57 is selected to be smaller than the diameter of curvature of the annular opening 65. With this arrangement, the circular valve portion 67 is normally seated on or held in sealing contact with the bottom 63 of the valve body 55 to prevent the entrance of air into the tube 10, as is best seen in FIG. 9.

Figure 12:
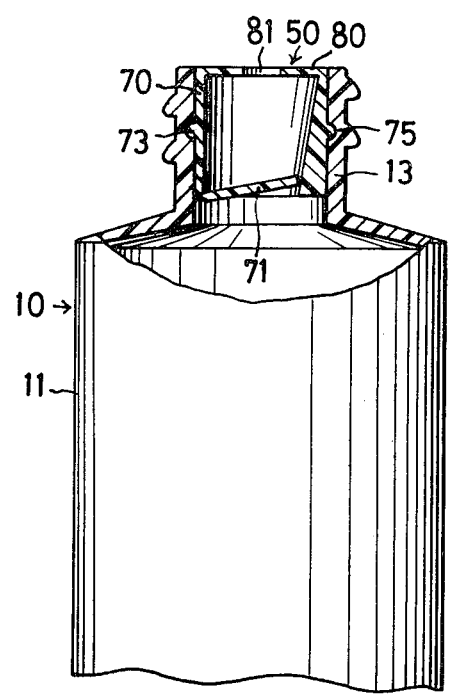
FIGS. 12, 13 and 14 show a further modification of the nonreturn valve.

FIG. 12 shows a further example of the non-return valve 50 having a unitary construction and which is preferably formed of a relatively soft plastic material. The non-return valve 50 includes a cylindrical portion 70 and a circular valve portion 71, the cylindrical portion 70 being fitted into the neck 13 of the tube 10. To prevent relative movements of the non-return valve 50 and the neck 13, a projection 73 is provided on the outer periphery of the cylindrical portion 70, which is received in a corresponding peripheral groove 75 formed in the inner surface of the neck 13.

Figure 13:
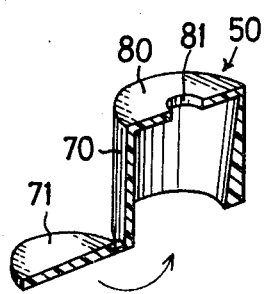
Figure 14:
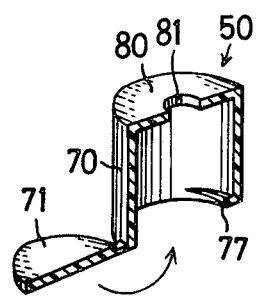

The valve portion 71 is formed integrally with the cylindrical portion 70. As is best seen in FIG. 13, the valve portion 71 is first formed so that it extends outwardly of the cylindrical portion 70, and thereafter is rotated in a counterclockwise direction to be inserted into the cylindrical portion 70. Since, as best seen in FIG. 12, the inner wall of the cylindrical portion 70 is somewhat converged towards its lower end, the valve portion 71 is brought into substantially sealing engagement with the inner wall when the valve portion 71 attempts to rotate in a clockwise direction due to its elasticity. Instead of having the inner wall converged, it would be possible to provide a projection 77 in the inner surface of the cylindrical portion 70 on the opposite side of the valve portion 71, as is shown in FIG. 14. In this embodiment also, the valve portion 71 is moved upwards or rotated in a counter-clockwise direction to open the non-return valve when the substance contained in the tube is squeezed out. Since the valve portion 71 is elastically connected to the cylindrical portion 70, if pressures developed inside the tube 10 are released, then the valve portion rotates in a clockwise direction, coming into substantially sealing contact with the inner wall or the projection 77.

The cylindrical portion 70 may be formed integrally with an orifice member 80 having a central opening 81 therein.

What is claimed is:

1. A collapsable container made of plastic comprising:
   a body comprising a tube with a lap joint, the wall of said tube being laminated and including an outer first water-resisting layer, an adjacent printable layer, an intermediate layer of a material selected from the group consisting of polyvinyl alcohol and an ethylene-vinyl alcohol copolymer, and an inner second water-resisting layer in the order named, the edge of said laminated wall inside said tube and adjacent said lap joint having a water-resistant deposit thereon to seal said inner edge;
   a head joined to one end of said body;
   a neck extending outwardly from said head, said neck being adapted to receive a closure member;
   whereby substances may be confined within said plastic container and protected from degradation caused by exposure to the atmosphere and by loss of volatile ingredients.

2. A collapsable container as set forth in claim 1, in which the first and second water-resisting layers are comprised of polypropylene.

3. A collapsable container as set forth in claim 1, in which the first and second layers are comprised of polyvinyl chloride.

4. A collapsable container as set forth in claim 1, in which the second water-resisting layer is approximately 1.5 to 4 times as thick as the first water-resisting layer.

5. A collapsable container as set forth in claim 1, in which the intermediate layer is coated with a coating of polyvinylidene chloride.

6. A collapsable container as set forth in claim 1, further comprising a non-return valve provided at the neck.

7. A collapsable container as set forth in claim 1, in which the first and second water-resisting layers are comprised of polyethylene.

8. A collapsable container as set forth in claim 7, in which the printable layer includes a layer of nylon.

9. A collapsable container as set forth in claim 7, in which the printable layer includes a sheet of paper coated on both surfaces thereof with polyethylene.

10. A collapsable container as set forth in claim 7, in which the printable layer includes a layer of oriented polypropylene.

11. A collapsable container as set forth in claim 10, in which the oriented polypropylene layer is coated on both surfaces thereof with coatings of polyvinylidene chloride.

12. A collapsable container as set forth in claim 10, in which the oriented polypropylene layer is coated on the surface thereof adjacent the first polyethylene layer with a coating of polyvinylidene chloride.

13. A collapsable container as set forth in claim 12, in which another oriented polypropylene layer is interposed between the intermediate layer and the second polyethylene layer, the oriented polypropylene layer being coated on the surface thereof adjacent the second polyethylene layer with a coating of polyvinylidene chloride.

14. A collapsable container as set forth in claim 7, in which the printable layer includes a layer of polyester.

15. A collapsable container as set forth in claim 14, in which the polyester film is coated on both surfaces thereof with coatings of polyvinylidene chloride.

16. A collapsable container as set forth in claim 14, in which the polyester film is coated on the surface thereof adjacent the first polyethylene layer with a coating of polyvinylidene chloride.

17. A collapsable container as set forth in claim 16, in which the polyester film is interposed between the intermediate layer and the second polyethylene layer, the polyester film being coated on the surface adjacent the second polyethylene layer with a coating of polyvinylidene chloride.

18. A collapsable container made of plastic comprising:
   a body comprising a tube with a lap joint, the wall of said tube being laminated and including an outer water-resisting layer, an adjacent printable layer, an intermediate layer of a material selected from the group consisting of polyvinyl alcohol and an ethylene-vinyl alcohol copolymer, and an inner water-resisting layer in the order named, the edge of said laminated wall inside said tube and adjacent said lap joint having a water-resistant deposit thereon to seal said inner edge;
   a head joined to one end of said body;
   a neck extending outwardly from said head, said neck being adapted to receive a closure member, and inside surface of said neck having an inward projection forming a valve seat; and
   a non-return valve comprising a circular flapper integrally hinged to said inside surface and being elastically held in sealing engagement with said valve seat, whereby substances may be confined within said plastic container and protected from degradation caused by exposure to the atmosphere and by loss of volatile ingredients.

19. A collapsable container made of plastic comprising:
   a body comprising a tube with a lap joint, the wall of said tube being laminated and including an outer water-resisting layer, an adjacent printable layer, an intermediate layer of a material selected from the group consisting of polyvinyl alcohol and an ethylene-vinyl alcohol copolymer, and an inner second water-resisting layer in the order named, the edge of said laminated wall inside said tube and adjacent said lap joint having a water-resistant deposit thereon to seal said inner edge;
   a head joined to one end of said body;
   a neck extending outwardly from said head, said neck being adapted to receive a closure member and having an inside surface; and
   a non-return valve comprising a valve body positioned adjacent said inside surface of said neck, said valve body having an inside surface and a bottom portion forming a valve seat and having a central opening forming a passageway, said valve further including a valve member positioned adjacent said inside surface of said valve body, said valve member having a bottom portion forming a flapper integrally hinged to said valve member to be held elastically against said valve seat, whereby substances may be confined within said plastic container and protected from degradation caused by exposure to the atmosphere and by loss of volatile ingredients.

20. A collapsable container made of plastic comprising:
   a body comprising a tube with a lap joint, the wall of said tube being laminated and including an outer water-resisting layer, an adjacent printable layer, an intermediate layer of a material selected from the group consisting of polyvinyl alcohol and an ethylene-vinyl alcohol copolymer, and an inner water-resisting layer in the order named, the edge of said laminated wall inside said tube and adjacent said lap joint having a water-resistant deposit thereon to seal said inner edge;
   a head joined to one end of said body;
   a neck extending outwardly from said head, said neck being adapted to receive a closure member and having an inside surface; and
   a non-return valve of unitary construction comprising an integral valve housing positioned adjacent said inside surface of said neck, and having a valve flapper integrally hinged to said housing and held elastically inwardly whereby substances may be confined within said plastic container and protected from degradation caused by exposure to the atmosphere and by loss of volatile ingredients.

21. A collapsable container as set forth in claim 20, wherein an inside surface of said valve housing is convergent inwardly, thus providing a seat for said flapper.

22. A collapsable container as set forth in claim 20, wherein an inside surface of said valve housing has an inward projection providing a seat for said flapper.

* * * * *